US008953037B2

(12) United States Patent
Wang et al.

(10) Patent No.: US 8,953,037 B2
(45) Date of Patent: Feb. 10, 2015

(54) OBTAINING SPATIALLY VARYING BIDIRECTIONAL REFLECTANCE DISTRIBUTION FUNCTION

(75) Inventors: Jiaping Wang, Beijing (CN); Baining Guo, Beijing (CN); Peiran Ren, Beijing (CN); John Michael Snyder, Redmond, WA (US); Xin Tong, Beijing (CN)

(73) Assignee: Microsoft Corporation, Redmond, WA (US)

( * ) Notice: Subject to any disclaimer, the term of this patent is extended or adjusted under 35 U.S.C. 154(b) by 566 days.

(21) Appl. No.: 13/274,191

(22) Filed: Oct. 14, 2011

(65) Prior Publication Data

US 2013/0093883 A1    Apr. 18, 2013

(51) Int. Cl.
  *H04N 9/47*      (2006.01)
  *H04N 1/00*      (2006.01)
  *G01N 21/55*     (2014.01)

(52) U.S. Cl.
  CPC ........... *H04N 1/00018* (2013.01); *G01N 21/55* (2013.01); *H04N 1/00013* (2013.01); *H04N 1/00045* (2013.01); *H04N 1/00087* (2013.01)
  USPC ....................................................... 348/142

(58) Field of Classification Search
  CPC .............. G01N 21/55; H04N 1/00013; H04N 1/00087; H04N 1/00045; H04N 1/00018
  USPC ......................................................... 348/142
  See application file for complete search history.

(56) References Cited

U.S. PATENT DOCUMENTS

| 6,738,569 | B1* | 5/2004 | Sogabe et al. ................... 396/21 |
| 6,930,681 | B2 | 8/2005 | Raskar et al. |
| 6,987,568 | B2* | 1/2006 | Dana ............................. 356/446 |
| 7,123,259 | B2 | 10/2006 | Cabral et al. |
| 7,230,620 | B2 | 6/2007 | Pfister et al. |
| 7,773,208 | B2 | 8/2010 | Piombini et al. |
| 8,248,473 | B2* | 8/2012 | Graber ........................... 348/153 |
| 2004/0179714 | A1* | 9/2004 | Jouppi ........................... 382/103 |
| 2009/0213120 | A1* | 8/2009 | Nisper et al. ................... 345/426 |
| 2010/0033721 | A1* | 2/2010 | Lee et al. ....................... 356/421 |
| 2010/0188290 | A1* | 7/2010 | Vacanti .......................... 342/385 |
| 2010/0277477 | A1 | 11/2010 | Wang et al. |

OTHER PUBLICATIONS

Tam, "Voronoi Ball Models for Computational Shape Applications", Thesis, The University of British Columbia, Feb. 2004, 143 pgs.

(Continued)

*Primary Examiner* — Dave Czekaj
*Assistant Examiner* — Leron Beck
(74) *Attorney, Agent, or Firm* — Dan Choi; Mila Sula; Mickey Minhas

(57) ABSTRACT

A system for reflectance acquisition of a target includes a light source, an image capture device, and a reflectance reference chart. The reflectance reference chart is fixed relative to the target. The light source provides a uniform band of light across at least a dimension of the target. The image capture device is configured and positioned to encompass at least a portion of the target and at least a portion of the reflectance reference chart within a field-of-view of the image capture device. The image capture device captures a sequence of images of the target and the reflectance reference chart during a scan thereof. Reflectance responses are calculated for the pixels in the sequence of images. Reference reflectance response distribution functions are matched to the calculated reflectance responses, and an image of the target is reconstructed based at least in part on the matched reference reflectance response distribution functions.

19 Claims, 8 Drawing Sheets

(56) References Cited

OTHER PUBLICATIONS

Alldrin et al, "Photometric Stereo With Non-Parametric and Spatially-Varying Reflectance", Conf on Comp. Vision and Pattern Recognition, 8 pgs.
An et al, "AppProp: All-Pairs Appearance-Space Edit Propagation", Journal ACM Transactions on Graphics, SIGGRAPH 2008, vol. 27, Issue 3, Aug. 2008, 9 pgs.
Ashikhmin et al, "A Microfacet-Based BRDF Generator", SIGGRAPH 2000, Proc 27th Annual ACM Conf on Computer Graphics and Interactive Techiques, , Jul. 2000, 10 pgs.
Ben-Ezra et al, "An LED-only BRDF Measurement Device", Jun. 2008, IEEE Conf on Computer Vision and Pattern Recognition, 8 pgs.
Chen et al, "Mesostructure from Specularity", Proc of Computer Vision and Pattern Recognition, IEEE, Jun. 2006, 8 pgs.
Cook et al, "A Reflectance Model for Computer Graphics", Computer Graphics, vol. 15, No. 3, Aug. 1981, 10 pgs.
Dana, "BRDF BTF Measurement Device", Proc 8th IEE Intl Conf on Computer Vision, Jul. 2001, 7 pgs.
Dana et al, "Reflectance and Texture of Real-World Surfaces", Journal ACM Transactions on Graphics, vol. 18, Issue 1, Jan. 1999, 34 pgs.
Debevec et al, "Acquiring the Reflectance Field of a Human Face", Proc 27th Annual Conf on Computer Graphics and Interactive Techniques, SIGGRAPH 2000, Jul. 2000, 12 pgs.
Dong et al, "Manifold Bootstrapping for SVBRDF Capture", ACM SIGGRAPH 2010, ACM Transactions on Graphics, vol. 29, No. 4, Jul. 2010, 9 pgs.
Gardner et al, "Linear Light Source Reflectometry", Proc ACM Transaction on Graphics, SIGGRAPH 2003, vol. 22, Issue 3, Jul. 2003, 10 pgs.
Garg et al, "Symmetric Photography: Exploiting Data-Sparseness in Reflectance Fields", Eurographics Workshop-Symposium on Rendering, Jun. 2006, 12 pgs.
Ghosh et al, "BRDF Acquisition with Basis Illumination", IEEE 11th Intl Conf on Computer Vision, Oct. 2007, 8 pgs.
Ghosh et al, "Circularly Polarized Spherical Illumination Reflectometry", ACM Transactions on Graphics, Proc ACM SIGGRAPH Asia, Dec. 2010, vol. 29, Issue 6, 12 pgs.
Ghosh et al, "Estimating Specular Roughness and Anisotrophy from Second Order Spherical Gradient Illumination", Computer Graphics Forum (Proc EGSR), Jun. 2009, vol. 28, No. 4, 10 pgs.
Goldman et al, "Shape and Spatially-Varying BRDFs From Photometric Stereo", 10th IEEE Intl Conf on Computer Vision, Oct. 2005, 8 pgs.
Han et al, "Measuring Bidirectional Texture Reflectance with a Kaleidoscope", ACM Transaction on Graphics, Proc ACM SIGGRAPH, Jul. 2003, vol. 22, Issue 3, 8 pgs.
Hertzmann et al, "Shape and Materials by Example: A Photometric Stereo Approach", Proc IEEE Conf on Computer Vision and Pattern Recognition, Jun. 2003, 8 pgs.
Holroyd et al, "A Coaxial Optical Scanner for Synchronous Acquisition of 3D Geometry and Surface Reflectance", Journal ACM Transactions on Graphics, Proc ACM SIGGRAPH 2010, Jul. 2010, vol. 29, Issue 4, 12 pgs.
Holroyd et al, "A Photometric Approach for Estimating Normals and Tangents", Journal ACM Transactions on Graphics, Proc ACM SIGGRAPH Asia 2008, Dec. 2008, vol. 27, Issue 5, 9 pgs.
Lawrence et al, "Inverse Shade Trees for Non-Parametric Material Representation and Editing", Jul. 2006, ACM Transactions on Graphics, Proc SIGGRAPH 2006, vol. 25, Issue 3, 12 pgs.
Lawson et al, Book titled "Solving Least Squares Problems", 1974, Chapt 23 titled Linear Least Squares with Linear Inequality Constraints, Section 3 Problem NNLS, p. 161.
Lensch et al, "Image-Based Reconstruction of Spatial Appearance and Geometric Detail", Apr. 2003, ACM Transactions on Graphics, vol. 22, No. 3, 27 pgs.
Lu et al, "Optical Properties (bidirectional reflection distribution functions) of Velvet", Sep. 1998, Applied Optics, vol. 37, No. 25, pp. 5974-5984.
Ma et al, "Rapid Acquisition of Specular and Diffuse Normal Maps from Polarized Spherical Gradient Illumination", Jun. 2007, Rendering Techniques, 18th Eurographics Symposium on Rendering, 12 pgs.
Marschner et al, "Image-Based BRDF Measurement Including Human Skin", 10th Eurographics Rendering Workshop, Jun. 1999, 15 pgs.
Matusik et al, "A Data-Driven Reflectance Model", Proc Intl Conf on Computer Graphics and Interactive Techniques, ACM SIGGRAPH, Jul. 2003, 12 pgs.
Matusik et al, "Efficient Isotropic BRDF Measurement", Jun. 2003, Proc 14th Eurographics Symposium on Rendering, 9 pgs.
Matusik et al, "Printing Spatially-Varying Reflectance", ACM Transactions on Graphics, Proc SIGGRAPH, Dec. 2009, vol. 28, Issue 5, 9 pgs.
McAllister et al, "Efficient Rendering of Spatial Bi-Directional Reflectance Distribution Functions", Sep. 2002, Proc 17th Eurographics, SIGGRAPH workshop on Graphics Hardware, 11 pgs.
Mukaigawa et al, "High-Speed Measurement of BRDF Using an Ellipsoidal Mirror and a Projector", Jun. 2007, IEEE Conf on Computer Vision and Pattern Recognition, 8 pgs.
Muller et al, "Acquisition, Synthesis and Rendering of Bidirectional Texture Functions", Mar. 2005, Computer Graphics Forum, vol. 24, No. 1, 26 pgs.
Ngan et al, "Experimental Analysis of BRDF Models", Jun. 2005, Eurographics Symposium on Rendering, 12 pgs.
"Optical Systems Design", Technical Programme, SPIE Eruope Intl Symposium, Sep. 2005, 84 pgs.
Ramamoorthi et al, "A Signal-Processing Framework for Inverse Rendering", Aug. 2001, Proc 28th Annual ACM Conf on Computer Graphics and Interactive Techniques, 12 pgs.
Romeiro et al, "Blind Reflectometry", Proc 11th European Conf on Computer Vision, Sep. 2010, 14 pgs.
Romeiro et al, "Passive Reflectometry", Oct 2008, Proc 10th European Conf on Computer Vision, 14 pgs.
Sakoe et al, "Dynamic Programming Algorithm Optimization for Spoken Word Recognition", Feb. 1978, IEEE Transactions of Acoustics, Speech and Signal Processing, 7 pgs.
Treuille et al, "Example-Based Stereo with General BRDFs", May 2004, 8th European Conference on Computer Vision, 13 pgs.
Wang et al, "All-Frequency Rendering of Dynamic, Spatially-Varying Reflectance", Dec. 2009, ACM Transactions on Graphics, Proc ACM SIGGRAPH, vol. 28, No. 5, 10 pgs.
Wang et al, "Modeling Anisotropic Surface Reflectance with Example-Based Microfacet Synthesis", Aug. 2008, ACM SIGGRAPH, Journal ACM Transactions on Graphics, vol. 27, Issue 3, 9 pgs.
Ward et al, "Measuring and Modeling Anisotropic Reflection", Jul. 1992, Proc 19th Annual AMC Conf on Computer Graphics and Interactive Techniques, 8 pgs.
Weyrich, "Acquisition of Human Faces Using a Measurement-Based Skin Reflectance Model", 2006, Ph.D. Thesis, Dissertation, 227 pgs.
Xu et al, "Efficient Affinity-Based Edit Propagation Using K-D Tree", Dec. 2009, Journal ACM Transactions on Graphics, vol. 28, Issue 5, SIGGRAPH, 6 pgs.
Xu et al, "Spherical Piecewise Constant Basis Functions for All-Frequency Precomputed Radiance Transfer", IEEE Transactions on Visualization and Computer Graphics, Mar. and Apr. 2008, vol. 14, No. 2, pgs. 454-467.
Zhang, "A Flexible New Technique for Camera Calibration", IEEE Transactions on Pattern Analysis and Machine Intelligence, vol. 22, No. 11, Nov. 2000, pp. 1330-1334.
Zickler et al, "Reflectance Sharing: Image-Based Rendering from a Sparse Set of Images", Jun. 2005, 16th Eurographics Symposium on Rendering, 12 pgs.
Ke, "A Method of Light Reflectance Measurement", Thesis, The University of British Columbia, Apr. 1999, 76 pgs.

* cited by examiner

OBTAINING SPATIALLY VARYING BIDIRECTIONAL REFLECTANCE DISTRIBUTION FUNCTION

BACKGROUND

An object's spatially varying reflectance is a complex, 6D function, which can be represented by its spatially varying bidirectional reflectance distribution function. Realistic reflectance is critical for convincing computer graphic rendering. Previously, capturing "realistic reflectance" from real world targets required expensive hardware and slow scanning and processing.

For example, a gonioreflectometer is a device that directly measures the bidirectional reflectance distribution function at a single surface point by densely sampling the angular domain of light and view directions. A single camera and light source can be moved to capture reflectance at multiple positions or multiple cameras and light sources may be mounted over a spherical dome. Other solutions leverage a curved mirror or a condenser lens. Direct measurement data have been increasingly employed in recent rendering and editing works.

Image-based methods capture a single bidirectional reflectance distribution function from a homogeneous curved surface of known geometry by varying directional lighting. Nondirectional lighting has also been applied.

Sparse views of a homogeneous sphere have been used to infer bidirectional reflectance distribution function and illumination.

Modeling an isotropic bidirectional reflectance distribution function as a general bivariate function of two angles (between normal and halfway vectors, and light and halfway vectors) can be employed to acquire a bidirectional reflectance distribution function from a single high dynamic range image of a homogeneous sphere and known environmental lighting captured by a light probe.

Most recently, statistical analysis of real-world illumination has been used to estimate a bidirectional reflectance distribution function from a single image of a homogeneous sphere under unknown lighting. Both reflectance and geometry of a homogeneous curved surface can be acquired by using a specialized coaxial optical scanner with spatially modulated light source.

These approaches all capture the bidirectional reflectance distribution function of a homogeneous surface of a target but cannot be easily extended to capture the bidirectional reflectance distribution function of a spatially varying surface of a target.

SUMMARY

This disclosure describes a simple, fast solution for reflectance acquisition using non-specialized devices such as non-specialized image capturing devices. An image capturing device such as a video camera captures video of a flat target surface illuminated by a moving light source such as a hand-held, linear light source. After processing, a spatially varying bidirectional reflectance distribution function is obtained. A bidirectional reflectance distribution function (BRDF) reference chart having a set of known bidirectional reflectance distribution function reference reflectors over a small card is provided. A sequence of light responses from the reference reflectors as well as from points on the target is captured and matched to reconstruct the target's appearance.

An algorithm for bidirectional reflectance distribution function reconstruction is provided. The algorithm may work directly on low dynamic range responses, without knowing the light or camera position, or acquiring high dynamic range lighting. The algorithm compensates for spatial variation caused by the local (finite distance) camera and light position by warping responses over time to align them to a specular reference. After alignment, a linear combination of the Lambertian and purely specular reference responses is found using a weighting to match each target point's response. The same weights may then be applied to the corresponding (known) reference bidirectional reflectance distribution functions to reconstruct the target point's bidirectional reflectance distribution function. The basic algorithm may also be extended to recover varying surface normals by adding two spherical caps for diffuse and specular references to the bidirectional reflectance distribution function chart.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

Overview

In one embodiment, a single-view image capture of a target and bidirectional reflectance distribution function (BRDF) reference chart is performed with an image capture device in conjunction with a dense 1D scan using a linear light source. A computing device may be configured to manipulate each pixel's 1D reflectance response directly without prior knowledge of the positions of the light source or image capture device, to simplify scanning. Reflectance is modeled using the reference reflectors which provide more realistic angular details than does a parametric model.

In some embodiments, methods disclosed herein capture more general spatially varying bidirectional reflectance distribution functions using a greater number of reflectance representatives, but on a flat target, than conventional example-based methods. In some embodiments, methods disclosed herein also handle local viewing and lighting.

Figure 1A:
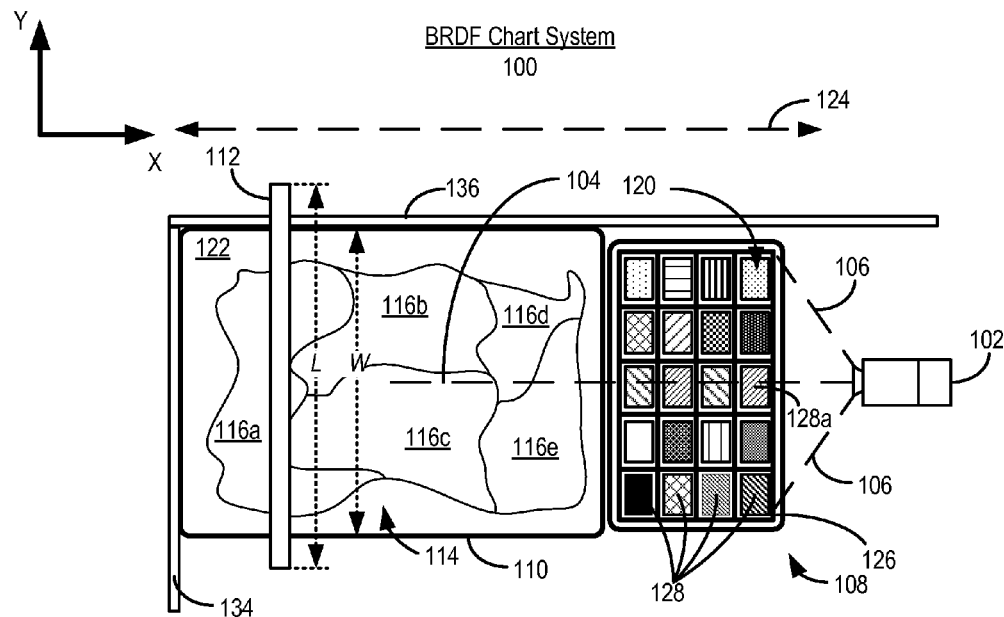
FIGS. 1A and 1B are a top view and a side view, respectively, of a bidirectional reflectance distribution function chart system according to one illustrated embodiment.
Figure 1B:
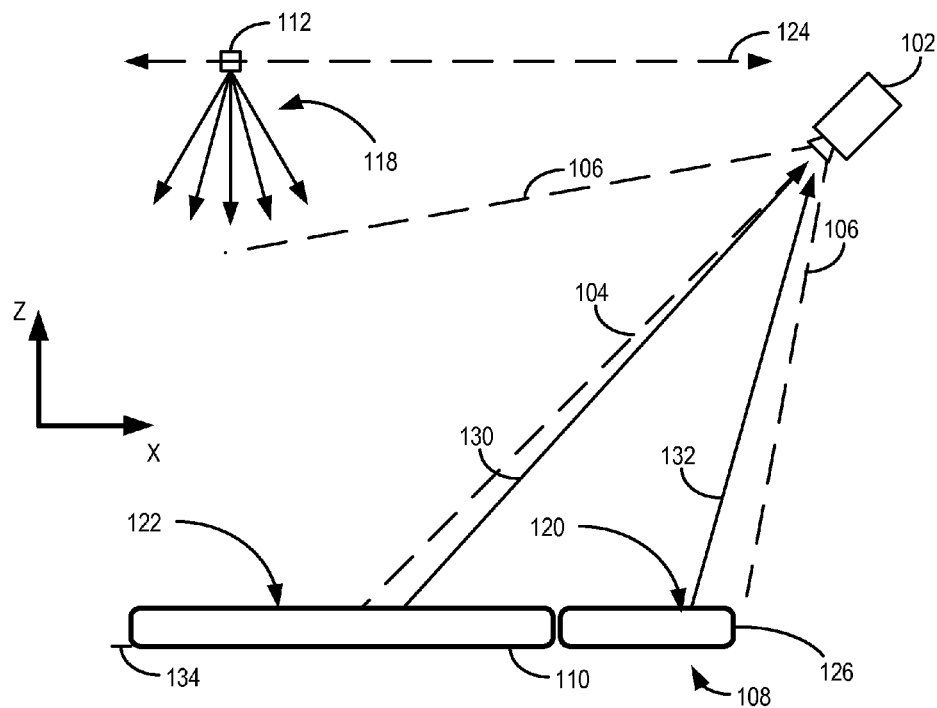

FIGS. 1A and 1B are top and side views of a Bidirectional Reflectance Distribution Function (BRDF) reference chart system 100, according to one illustrated embodiment. For the sake of clarity, the top view of the BRDF reference chart system 100 is given with respect to an X-Y plane and the side view is given with respect to an X-Z plane of a Cartesian coordinate system.

The BRDF reference chart system 100 includes an image capture device 102 having an optical axis 104 and a field-of-view 106. The image capture device 102 may be a video camera or other such device configured to capture multiple images. In some embodiments, the image capture device 102 may be a handheld device. In some embodiments, the image capture device 102 may be capable of being handheld but may be coupled to a mounting device. For example, the image capture device 102 may be a video camera, and the video camera may in some examples be mounted to a tripod or similar device. In some examples, the image capture device 102 may be a video camera of a smart phone or tablet, and the smart phone or tablet, may in some examples be mounted to a supporting device such as a smart phone car mount with a flexible stand. Typically, careful adjustment of the image capture device 102 is not required. For example, default settings, uncontrolled auto-exposure, and white-balance on devices such as smart phone video cameras work well. Of course, a high resolution camera may be used to obtain high spatial detail in the resulting spatially varying bidirectional reflectance distribution function. However, in some embodiments, a smart phone video camera capturing images at 1280×720 video at 30 frames-per-second (fps) may be sufficient.

The BRDF reference chart system 100 further includes a BRDF reference chart 108, a target 110, and a light source 112. The BRDF reference chart 108 and the target 110 are positioned within the field-of-view of the image capture device 102 and are aligned in a plane.

The target 110 includes a pattern 114. The pattern 114 is made up of multiple regions, individually referenced as 116a-116e and collectively referenced as 116. Typically, regions 116 may have non-uniform optical characteristics such as reflectance. Differences between the optical characteristics of the regions 116 may be due to one or more, but not limited to, the following: color, material, texture, finish, etc.

The light source 112 is movably positioned above the BRDF reference chart 108 and the target 110 and provides illumination (I) 118 onto top surfaces 120 and 122, respectively. In this embodiment, the light source 112 is moved in a direction denoted by dashed line 124, which is generally parallel to x-axis. The light source 112 may be a linear light source such as a fluorescent tube having a length (L). In some embodiments, the light source 112 may be a handheld, battery powered, fluorescent tube. However, the light source 112 may alternatively include an array of light emitters such as, but not limited to, light emitting diodes, incandescent lights, etc.

Typically, in the configuration shown in FIGS. 1A and 1B, the length (L) of the light source 112 is greater than a greatest width (W) (along the y-axis) of the BRDF reference chart 108 and the target 110. However, in other embodiments, the length (L) of the light source 112 may be less than a greatest width (W) (along the y-axis) of the BRDF reference chart 108 and the target 110. Typically, the light source 112 is sized, shaped and positioned to provide a uniform band of light over at least the width (W) (along the y-axis) of the BRDF reference chart 108 and the target 110. In other words, the illumination (I) 118 is uniform along the length (L) of the light source 112.

The BRDF reference chart 108 may comprise a palette 126 of known reference reflectors 128 used as representatives for reconstruction. The BRDF reference chart 108 illustrated in FIG. 1A contains twenty (20) reference reflectors 128. However, the number and arrangement of the reference reflectors 128 can vary. In some embodiments, a reference reflector 128 may be about 0.5 mm thick and may be affixed to the palette 126 by an adhesive such as glue. The palette 126 may be a material such as plastic, and in some embodiments, the palette 126 may include a 4 mm thick plastic base. In some embodiments, the BRDF reference chart 108 may measure approximately 8.5 cm×5.5 cm, little bigger than a credit card. However, the size of the BRDF reference chart 108 may be larger or smaller, in either or both of the x-direction and the y-direction, in other embodiments.

The BRDF reference chart 108 may contain two or more material types. For example, reference reflector 128a may be of a first material type and remaining ones of the reference reflectors 128 may be of at least one other material type. The reference reflector 128a may be a nearly ideal Lambertian material that provides a diffuse reference and may also be used to calibrate the exposure and white balance of the image capture device 102. In some embodiments, the reference reflector 128a may be a material of the Spectralon diffuse standard (albedo=80%) from Labsphere, Inc., in which the top surface 120 may have a surface area of approximately 1 cm2. The rest of the reference reflectors 128, may also have a surface area of 1 cm2, and may comprise different specular materials. In other embodiments, the reference reflectors 128 may have various size and shapes, e.g., square, rectangular, circular, oval, ellipsoid, triangular, etc.

The image capture device 102 captures light 130, 132 reflected from the target 110 and the BRDF reference chart 108, respectively, as the light source 112 is moved. The image capture device 102 captures a single-view and performs a dense 1D scan using the light source 112. In some embodiments, the image capture device 102 includes memory devices (not shown) for storing the captured images. In other embodiments, the image capture device 102 may be communicatively coupled to a memory device for storing captured images.

The BRDF reference chart system 100 may further include reference markers 134 and 136, which are generally aligned along the y-direction and x-direction, respectively. The reference markers 134, 136 include indicia from which relative positions of the BRDF reference chart 108 and the target 110 may be determined. From knowledge of the position of the BRDF reference chart 108, the positions of the reference reflectors 128 may also be determined.

Figure 1C:
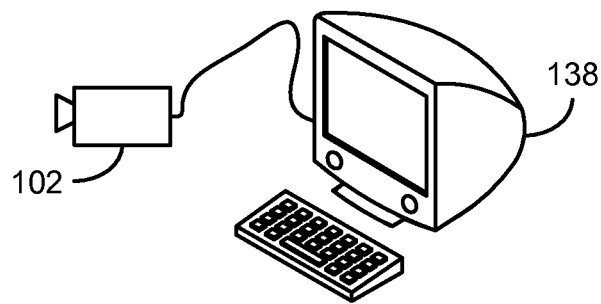
FIG. 1C is a schematic diagram of an illustrative environment for obtaining a reflectance distribution function according to one illustrated embodiment.

Referring to FIG. 1C, the image capture device 102 is communicatively coupled to a computing device 138 such as a personal computer, laptop computer, desktop computer, mobile computer, workstation, server, main frame, server farm, data center, or the like. The computing device 138 includes a storage device in which some or all of the images captured by the image capture device 102 are stored. The computing device 138 also includes one or more of hardware, firmware, and software for implementing algorithms to processing the captured images.

Figure 2A:
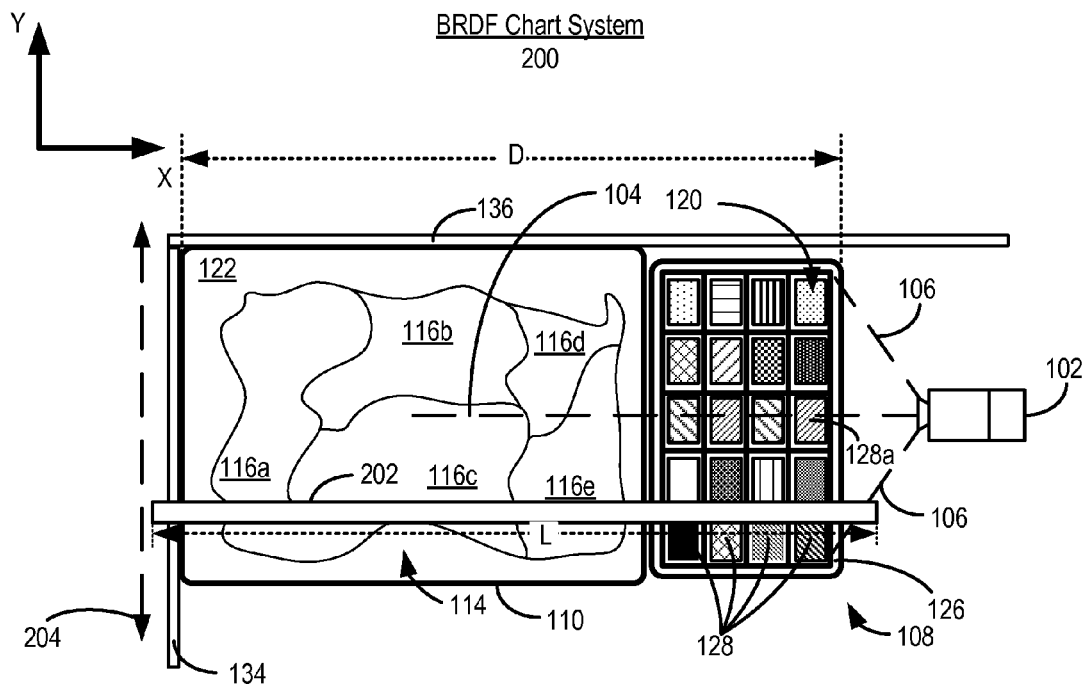
FIGS. 2A and 2B are a top view and a side view, respectively, of a bidirectional reflectance distribution function chart system according to another illustrated embodiment
Figure 2B:
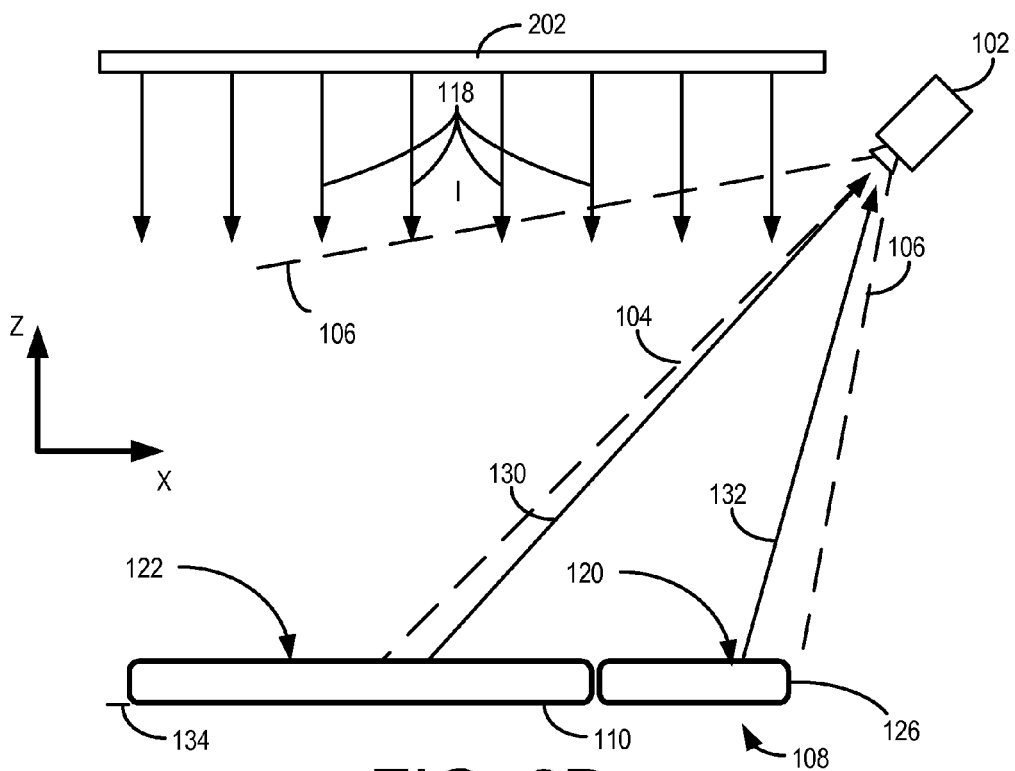

FIGS. 2A and 2B are a top view and a side view of a BRDF reference chart system 200, respectively, according to another embodiment. For the sake of clarity, the top view of the BRDF reference chart system 200 is given with respect to an X-Y plane and the side view is given with respect to an X-Z plane of a Cartesian coordinate system.

The BRDF reference chart system 200 includes the image capture device 102, the BRDF reference chart 108, the target 110, and an light source 202. The BRDF reference chart 108 and the target 110 are positioned within the field-of-view of the image capture device 102 and are aligned in a plane.

The light source 202 is movably positioned above the BRDF reference chart 108 and the target 110 and provides illumination (I) 118 onto top surfaces 120 and 122, respectively. In this embodiment, the light source 202 is moved in a direction, which is generally parallel to the y-axis, denoted by dashed line 204 (see FIG. 2A). The light source 202 may be a linear light source such as a fluorescent tube having a length (L). In some embodiments, the light source 202 may be a handheld, battery powered, fluorescent tube. However, the light source 202 may alternatively include an array of light emitters such as, but not limited to, light emitting diodes, incandescent lights, etc.

Typically, in the configuration shown in FIGS. 2A and 2B, the length (L) of the light source 202 is greater than a greatest distance (D) (along the x-axis) of the combination of the BRDF reference chart 108 and the target 110. However, in other embodiments, the length (L) of the light source 202 may be less than the greatest distance (D) (along the x-axis) of the combination of the BRDF reference chart 108 and the target 110. Typically, the light source 202 is sized, shaped and positioned to provide a uniform band of light over at least and the target 110. In other words, the illumination (I) 118 is uniform along the length (L) of the light source 202.

Figure 3A:
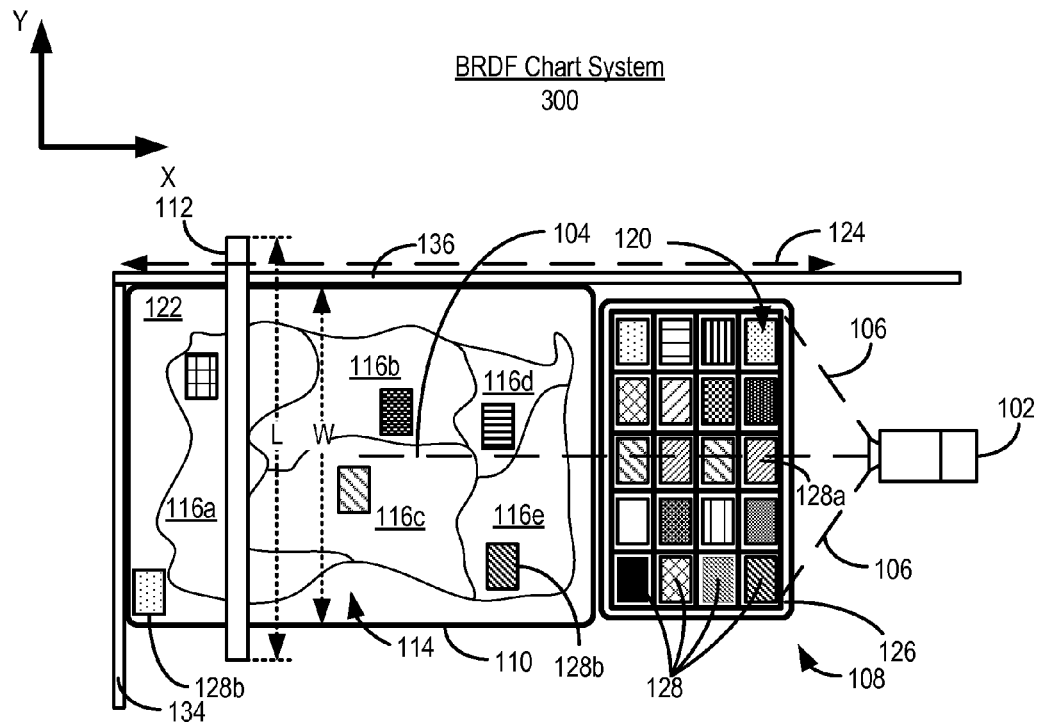
FIGS. 3A and 3B are a top view and a side view, respectively, of a bidirectional reflectance distribution function chart system according to another illustrated embodiment.
Figure 3B:
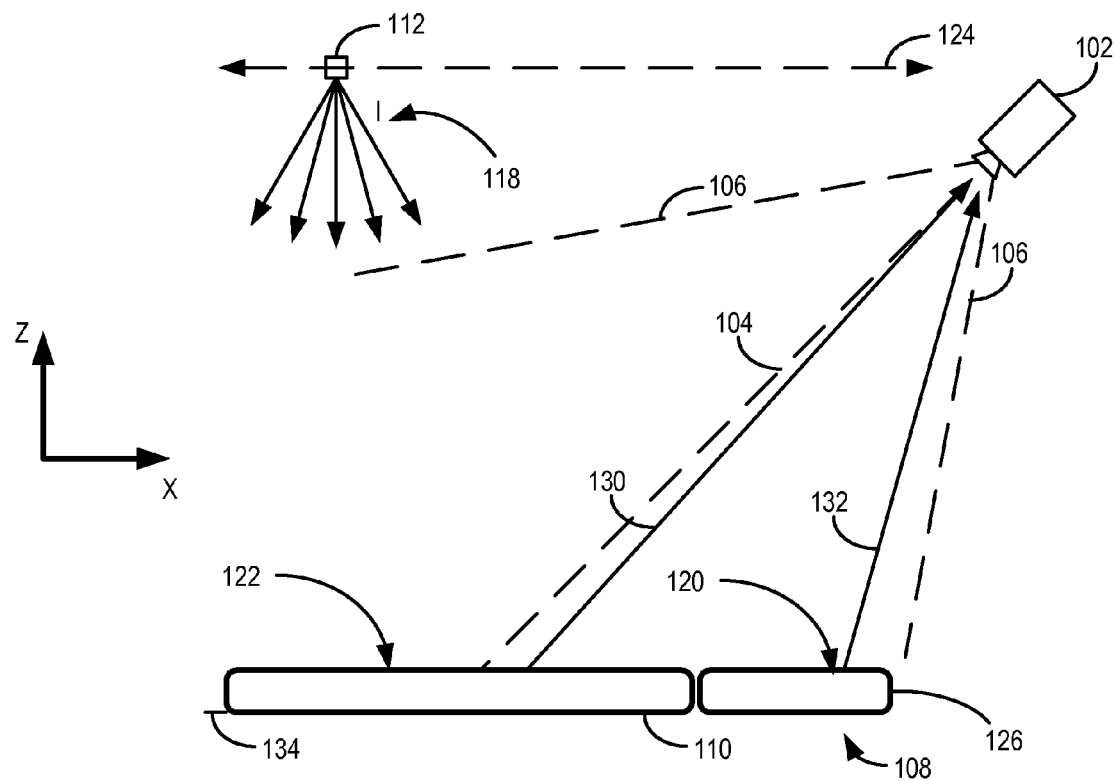

FIGS. 3A and 3B are a top view and a side view of a BRDF reference chart system 300, respectively, according to another embodiment. For the sake of clarity, the top view of the BRDF reference chart system 300 is given with respect to an X-Y plane and the side view is given with respect to an X-Z plane of a Cartesian coordinate system.

In the embodiment illustrated, a number of reference reflectors 128b are positioned at various known locations of the target 110. Typically, the reference reflectors 128b are positioned in regions 116 that are generally uniform in optical characteristics such that the reference reflectors 128b can be digitally edited out of images captured by the image capture device 102.

Figure 4A:
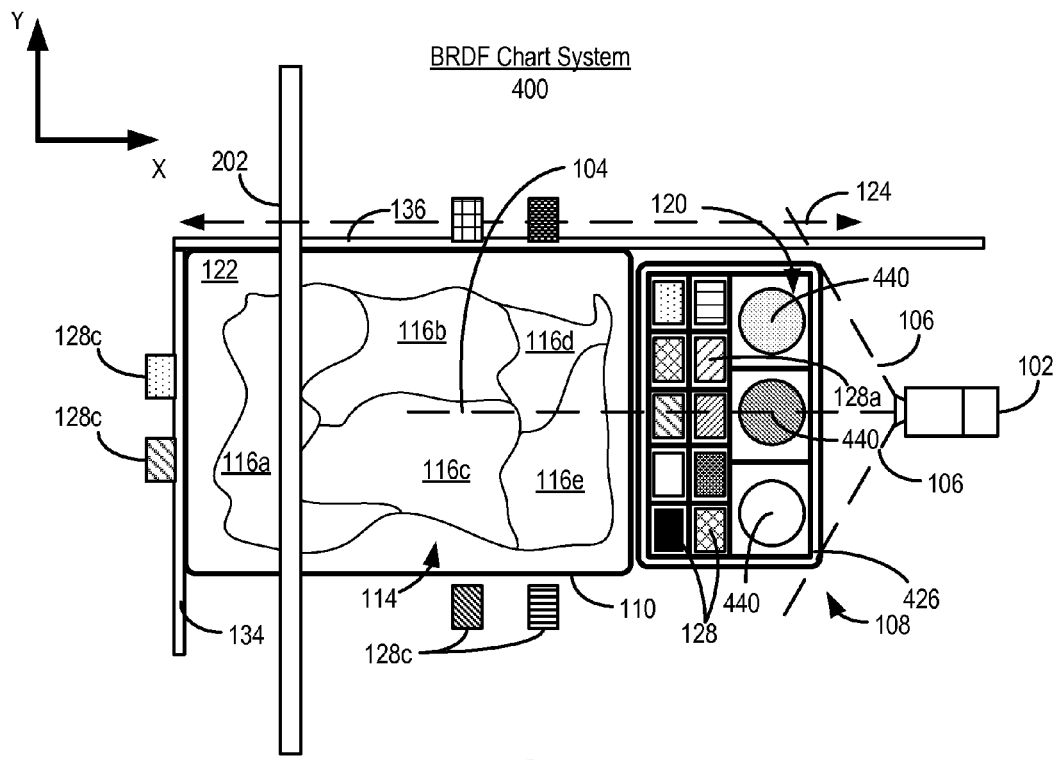
FIGS. 4A and 4B are a top view and a side view, respectively, of a bidirectional reflectance distribution function chart system according to another illustrated embodiment.
Figure 4B:
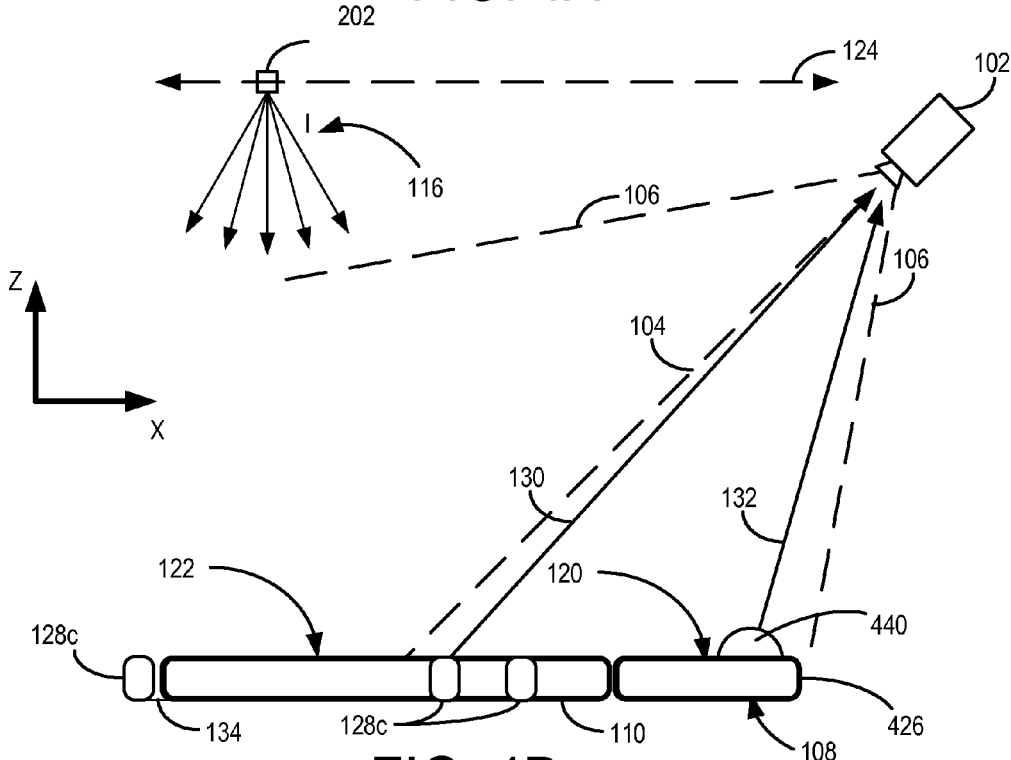

FIGS. 4A and 4B are a top view and a side view of a BRDF reference chart system 400, respectively, according to another embodiment. For the sake of clarity, the top view of the BRDF reference chart system 400 is given with respect to an X-Y plane and the side view is given with respect to an X-Z plane of a Cartesian coordinate system.

In the embodiment illustrated, a number of reference reflectors 128c are positioned, at various known locations, outside of the target 110.

A palette 426 includes a number of non-planar reference reflectors 440. In the illustrated embodiment, the non-planar reference reflectors 440 are shown as a being generally spherically cap shaped, in which a spherical cap corresponds to a portion of a sphere that is less than a hemisphere. However, the non-planar reference reflectors 440 are not limited to generally spherically cap shapes.

In this embodiment, the light source 202 may be scanned over the BRDF reference chart 108, the reference reflectors 128c and the target 110 in both the x-direction and the y-direction. If the light source 202 is scanned in both directions, the light source 202 is sized, shaped and positioned to provide a uniform band of light over at least a portion of the BRDF reference chart 108, the reference reflectors 128c and the target 110 during both scans.

Example Bidirectional Reflectance Distribution Function Model

In calculating the bidirectional reflectance distribution function model herein, the 3D unit vectors i (incoming) and o (outgoing) denote the light and view direction, respectively. A bidirectional reflectance distribution function $\beta$ is represented as a linear combination of a normalized Lambertian bidirectional reflectance distribution function cc and a normalized specular bidirectional reflectance distribution function $\beta$ shared by all three color channels, via $$\rho(i, o) = d\alpha(i, o) + s\beta(i, o), \qquad (1)$$

$$\alpha(i, o) = \frac{1}{4\pi^2}, \int_{\Omega+}\int_{\Omega+} \beta(i, o)\,di = 1, \qquad (2)$$

where, $\int_{\Omega+}\beta(i,o)di \leq 1$, and $d \geq 0$ and $s \geq 0$ are three-channel diffuse and specular coefficients, respectively. While the normalized Lambertian bidirectional reflectance distribution function $\alpha$ is constant, the normalized specular bidirectional reflectance distribution function $\beta$ is complex and affected by several factors, including surface roughness, Fresnel reflection, and shadowing, that cause nonlinear variation over the target. This specular variation is assumed to form a low-dimensional manifold which can be reconstructed by local linear embedding using a limited number of representatives. A set of bidirectional reflectance distribution function chart samples is denoted as $\{\rho_i\}$, with corresponding normalized specular components $\phi = \{\beta_i\}$. The model represents the bidirectional reflectance distribution function $\rho(x)$ at each surface point x using overall diffuse and specular coefficients and a local linear combination over $\phi$, via $$\rho(x) = d(x)\alpha + s(x)\Sigma_{j=1}^{k} u_j(x)\beta_j, \beta_j \in \phi(\beta), \qquad (3)$$

where $\phi(\beta)$ denotes the k-nearest neighbors in $\phi$ of the normalized specular part of $\beta(x)$. The weights $u_j(x)$ are non-negative and sum to 1, for each x. In some implementations, k=8.

Example Bidirectional Reflectance Distribution Function Chart Design

Representative bidirectional reflectance distribution functions on the reflectance reference chart 108 are chosen to permit the reconstruction of different targets. An algorithm that computes a set of representatives from a given bidirectional reflectance distribution function database of interest is discussed below. In some embodiments, the computation is based only on normalized specular bidirectional reflectance distribution function components and ignores variation in diffuse and specular coefficient, which is handled separately.

Given a set of normalized specular bidirectional reflectance distribution functions $\{\beta_i\}$, a subset $\psi$ for which local linear embedding can accurately reconstruct any member of the database is chosen. A k-nearest neighbor graph for the database is constructed first, and the most distant pair of samples $\{\beta_1, \beta_2\}$ based on greatest geodesic distance in the graph is found. Next, 2 k additional samples are selected by iteratively picking the sample having the maximum geodesic distance to all samples accumulated so far. Beyond these, each further sample is chosen that has maximum reconstruction error from equation 3. The error is measured by the weighted L2-norm:

$$E^2 = \frac{\int_{\Omega+}\int_{\Omega+}(i, n)^2(\beta^*(i, o) - \beta(i, o))^2 \, di \, do}{\int_{\Omega+}\int_{\Omega+}(i, n)^2 \, di \, do}, \quad (4)$$

where n is the surface normal. Then (physical) material tiles or reference reflectors 128 for the selected representatives are placed on the bidirectional reflectance distribution function reference chart 108.

In experiments, based on a bidirectional reflectance distribution function database of one hundred (100) homogeneous isotropic materials, the above computation was performed using an error threshold of 2.5% to obtain 24 bidirectional reflectance distribution function chart representatives or reference reflectors 128.

These materials were measured with a gonioreflectometer. The gonioreflectometer densely sampled the 1D polar angle of lighting direction with a fixed camera. The light source was 2 meters away from the material and the camera was about 1 meter away. The camera was tilted at about 45 degrees and its precise position was calibrated before data capturing. Positions of the moving light source were determined by precision mechanical control. Ninety (90) images were uniformly sampled while the light source moves from top (q)=0° to bottom (q)=90°, which took about ten minutes. The captured data was then fit using a general micro facet BRDF model with a tabulated 1D normal distribution function. The specular component was separated by subtracting the minimum reflectance value from the measured BRDF.

Example Data Capture and Preprocessing

In some embodiments, the target 110 may be flat and may be positioned in the XY plane with its center at the origin. A typical target 110 may measure approximately ten by ten centimeters (10 cm×10 cm).

The image capture device 102 may be placed approximately fifty centimeters (50 cm) away from the origin along the X axis and 40 cm above it, making an angle of roughly 40 degrees with the Z axis. The BRDF reference chart 108 may adjoin the target in the Y direction. The light source 112 may be positioned one hundred centimeters (100 cm) above the target 110 and the BRDF reference chart 108, with its length (L) aligned with the Y-direction. The light source 112 may be moved back and forth from approximately X=−100 cm to X=20 cm. Typically, the above measurements may be approximated, and the light movement need not be controlled accurately. In some embodiments, approximately thirty (30) seconds of image capturing is performed by the image capture device 102 during the movement of the light source 112 and this generates an image sequence of approximately nine hundred (900) images.

The image sequence is processed by first calibrating intensity based on a pre-computed gamma (power law) curve for the response of the image capture device 102. Reflected light from the background environment is removed by subtracting a frame with the light source 112 turned off and/or not illuminating the target 110 and the BRDF reference chart 108. This yields a partially-calibrated image sequence denoted by ř(t). Reflectance responses depend on the target location x. (The notation used herein makes that dependence implicit.)

The partially-calibrated image sequence is divided by the image sequence of the Lambertian reference reflector 128a, ř*(t), at each time sample t:

$$\tilde{r}(t) = \frac{\check{r}(t)}{\check{r}_*(t)} \quad (5)$$

This compensates for time-varying camera exposure, lighting distance variation, and approximate cosine factor in the radiance integral. The resulting ř(t) is referred to as the calibrated image sequence.

Example Reflectance Sequence Alignment

An alignment algorithm for reflectance responses based on dynamic time warping solves difficulties in matching reflectance responses captured on the target and chart. Variations caused by local view and light position can be approximately matched by shifting and possibly scaling the 1D reflectance sequence in time. For robust matching, response sequences may be normalized and their saturated samples repaired before the alignment.

Directional Variation as Time Shifting

The BRDF reference chart systems 100, 200, 300, and 400 may imply variation of light and view direction over the BRDF reference chart 108 and the target 110. Responses captured at two different points thus differ even when their reflectance is identical. Sequences are matched by assuming that reflectance is isotropic and mainly determined by the half-vector, h, midway between the light and view directions. This assumption is suggested by the micro facet model after neglecting smooth factors based on shadowing (S) and Fresnel effects (F):

$$\rho(i, o) = \frac{S(i, o)F(i, o)N(h)}{4(i \cdot o)(o \cdot h)} \quad (6)$$

where h=(i+o)/∥i+o∥ oil and n is the surface normal. An isotropic bidirectional reflectance distribution function further restricts the normal distribution function (NDF), N, to be a 1D function of angle, θ, between h and n.

Because a linear light source is held parallel over a flat acquisition target, each time point in the moving light scan yields just a small range for (well-lit) θ, at each target point x. But this dominant angle varies as a function of x because of light/view locality.

Detailed processing steps are explained in the following sections.

Normalization

The calibrated responses are normalized to eliminate the effect of a spatially-varying albedo, via $$\hat{r}(t) = \frac{\tilde{r}(t) - \tilde{r}_{min}}{\tilde{r}_{max} - \tilde{r}_{min}}, \quad (7)$$

where ř$_{min}$ and ř$_{max}$ are the minimal and maximal values of ř(t). For robustness, minimal/maximal values are determined by averaging over the 10 values of least/greatest magnitude. The resulting normalized sequence, ř(t), is used as input for alignment.

Saturated values are replaced with an estimate generated by fitting a 1D Gaussian to neighboring, non-saturated values. The fitting uses 10 to 20 samples on each side. This is done before the above normalization and only for matching. It has no further effect on bidirectional reflectance distribution function reconstruction, which blends previously-measured representatives.

Alignment by Dynamic Time Warping

Dynamic Time Warping (DTW) is used in time-series analysis for measuring similarity or aligning two discrete sequences. Given a reference sequence p(t) of length n (to warp to) and a source sequence q(t) of length m (to warp from), the algorithm seeks a pair of corresponding warp functions, $(w_p(t), w_q(t))$ that minimize the sum of element-wise differences between them:

$$\min_{w_p, w_q} \sum_{t=1}^{h} D(p(w_p(t)), q(w_q(t))), \tag{8}$$

where h is the common length of the two sequences after warping. This amounts to finding a minimal path from (1,1) to (n,m) in the n×m discrete 2D domain where each grid point (i, j) represents distance between p(i) and q(j).

The problem can be solved by dynamic programming. A distance function tailored to the application of matching reflectance responses is used:

$$D(p(i), q(j)) = (p(i)^\gamma - q(j)^\gamma)^2 + \lambda C_m, \tag{9}$$

where p and q are two normalized 1D reflectance sequences. The first term attempts to align specular peaks. A power function is used to suppress non-peak values. In one example, the value of $\gamma$ can be set to 3. The second term $C_m$ penalizes temporal shrinking or expansion (scaling). A small weight $\lambda$, for example, equal to 1% of the average intensity, which avoids undue scaling in noisy but low-amplitude regions may be used. To preserve the falloff shape of the source sequence's specular peak, no stretching in regions where the intensity exceeds 50% of its maximum is permitted.

The resulting warps are applied to align q to p, via $$q(t) = q(w_{q \to p}(t)), w_{q \to p}(t) = w_q(w_p^{-1}(t)). \tag{10}$$

The aligned sequence is finally resampled to the frame rate of the original video.

To obtain a canonical peak layout for bidirectional reflectance distribution function reconstruction, the reflectance sequences of all pixels are aligned to a single specular tile on the bidirectional reflectance distribution function chart. In some embodiments, the one having the highest unsaturated response peak is selected.

The resulting aligned sequence is denoted r(t) (without tilde or hat) and the corresponding time-sampled vector as r. Essentially, DTW provides a robust method of recentering each sequence around the peak of the canonical reference sequence chosen above.

Bidirectional Reflectance Distribution Function Reconstruction

After alignment and resampling, the resulting reflectance sequences r(t) are effectively responses from the same, infinitely-distant but time-varying environmental lighting {We, t=1, 2, ..., n} and a constant view direction, o. The resulting sequence thus characterizes the bidirectional reflectance distribution function at each target point and is called a reflectance vector. Reflectance vectors comprise h components, where h is about 900.

The reflectance function r(t) at some location is given by $$r(t) = \int_{\Omega^+} L_t(i)[d\alpha(i,o) + s\beta(i,o)](n \cdot i) di. \tag{11}$$

The diffuse and specular terms are separated to yield $$r = da + sb, \tag{12a}$$

$$a(t) = \int_{\Omega^+} L_t(i)\alpha(i,o)(n \cdot i) di, \beta(t) = \int_{\Omega^+} L_t(i)\beta(i,o)(n \cdot i) di, \tag{12b}$$

where reflectance vectors a and b represent purely diffuse and specular responses, respectively.

The normalized reference diffuse response is given by $a = r_*/d_*$ where $r_*$ is the response of the Lambertian reference tile and $d_*$ is its albedo. The normalized specular response for reference material j is then given by $$b_j = \frac{r_j - d_j a}{s_j}, \tag{13}$$

where $r_j$ is the reference's aligned response and $d_j$ and $s_j$ are its diffuse and specular coefficients.

To reconstruct an unknown bidirectional reflectance distribution function $\rho$ with its measured reflectance vector r, the reconstruction error is minimized via $$\min_{u_0, u_1, \ldots, u_k} \left\| r - u_0 a - \sum_{j=1}^{k} u_k b_j \right\|, u_j \geq 0, b_j \in \Phi(r). \tag{14}$$

Given the set of r's nearby reference responses, $\phi(r)$, the above is a well-conditioned least squares problem with k+1 unknowns and h equations (h>>k). To ensure non-negativity in the weighting, equation (14) may be solved by quadratic programming with non-negative parameter constraints if negative values appear in the unconstrained least-squares solution.

Since the neighborhood is unknown, all possible representative neighborhoods may be tried. These may be pre-computed by randomly generating convex linear combinations of reference specular responses and finding their k-nearest neighborhood sets. In some embodiment 10,000 combinations may be tried, resulting in about 20 unique neighborhoods for k=8.

Saturated values in reflectance vectors cause problems when solving Equation 14. Since the equations are already highly constrained, any saturated components in the vectors r and $b_j$ can be eliminated. Typically, only 1-3% of the roughly 900 components are removed.

Equation 14 can be applied separately to the reflectance sequences of each color channel. This result yields significant color noise. A more robust color estimate may be obtained by first computing an RGB diffuse and specular coefficient and then solving for the linear combination of references. This shares the same specular falloff shape among all three channels.

An average over the 10 values of least brightness in the RGB sequence can be used to obtain the diffuse component $(d_r, d_g, d_b)$, and an average over the 10 greatest brightness samples can be used to get the specular component $(s_r, s_g, s_b)$. The diffuse coefficient is then normalized: $(d_r, d_g, d_b) = (d'_r, d'_g, d'_b)/\|(d'_r, d'_g, d'_b)\|$. The specular coefficient is likewise normalized via $$(s_r, s_g, s_b) = \frac{(s'_r, s'_g, s'_b) - (d'_r, d'_g, d'_b)}{\|(s'_r, s'_g, s'_b) - (d'_r, d'_g, d'_b)\|}. \tag{15}$$

The estimated RGB coefficients are substituted into Equation 14 to solve $$\min_{u_0, u_1, \ldots, u_k} \left\| \begin{bmatrix} r_r \\ r_g \\ r_b \end{bmatrix} - u_0 \begin{bmatrix} d_r \\ d_g \\ d_b \end{bmatrix} a - \begin{bmatrix} s_r \\ s_g \\ s_b \end{bmatrix} \sum_{j=1}^{k} u_k b_j \right\|, \quad (16)$$

$$u_j \geq 0, \, b_j \in \Phi(r).$$

Bumpy Surface Extension

Referring to FIGS. 4A and 4B, the non-planar reference reflectors 440 may be used to recover normal variation. The non-planar reference reflectors 440 may include one Lambertian reference reflector and one specular reference reflector to provide the corresponding responses for a range of surface orientations. Response at every target point is then matched with those from different points on the spherical cap references; the best match determines the normal.

In one embodiment, an exemplary method for matching reflectance may be based on temporal warping of reflectance responses to obtain a metric that is largely material-invariant, and so the method does not rely on references whose reflectance must closely match reflectance of the target. This is because pixels on the spherical cap have identical reflectance (specular lobe shape) and differ only in their responses' peak location, while DTW provides a robust way of aligning each sample's pixel response, of arbitrary reflectance, to these references.

For robust normal recovery, the light source 202 is scanned in both the X direction and in the Y direction. Two-axis light scanning distinguishes what is an intrinsically 2D (unit) surface normal.

Each point's surface normal is initialized to the best-matching Lambertian reference. A distance metric, based on an inner product, is applied:

$$\max_{j} \frac{\check{r} \cdot \check{r}_j}{\|\check{r}\| \|\check{r}_j\|}, \quad (17)$$

where $\check{r}$ is the reflectance sequence to be matched and $\check{r}_j$ are the candidate Lambertian reference sequences at different normals. Note that partially calibrated sequences $\check{r}$ are used here instead of (fully) calibrated ones since the surface orientation is unknown. This simple method suffices to recover normals at nearly diffuse target points. Points that are more specular may be processed further as described in the following. A point is deemed specular if its maximum value is 10% larger than its average, after dividing by the diffuse reference sequence with the best-matching normal.

Like bidirectional reflectance distribution function reconstruction, normal recovery for a specular point is based on its calibrated sequence r. But in this case, it should be normalized by dividing it by the sequence from the diffuse non-planar reference reflectors 440 having the same normal. Since that normal is unknown, an iterative procedure is applied. Normalization based on the previous step's normal is performed, and then this normalized response is matched against the non-planar reference reflectors 440 reference using a material-invariant metric from the DTW algorithm, which measures overall temporal distortion from the target sequence p(t) to the reference q(t) via $$\frac{1}{n} \sum_{t=1}^{n} \left( \frac{t-1}{n-1} - \frac{w_{q \to p}(t)}{n-1} \right)^2, \quad (18)$$

where $w_{q \to p}$ is the warp function from source to reference sequence defined in Equation 10. This metric cares only about the position of the specular peak and ignores its height and falloff. The chosen normal corresponds to the reference having minimum temporal distortion. These two steps (first, intensity-normalize by the Lambertian response of the previous step's normal, and second, select the specular reference normal having minimum distortion) are iterated until convergence, usually in 2-5 steps.

The above implies a binary decision: a point is either diffuse or specular. To suppress spatial artifacts from a hard boundary, blending between the two recovered normals, $n_d$ and $n_s$, can be performed, for most diffuse points that have maximum value 5-15% larger than the average. The blend is based on estimated specularity $\eta$ of the material, via $$n = (1 - \eta)n_d + \eta n_s, \, \eta = P\left(\lambda \left(\frac{\tilde{r}_{max}}{\tilde{r}_{avg}} - 1.1\right)\right), \quad (19)$$

where P is the sigmoid function switching from 0 to 1, and $\tilde{r}_{avg}$ denotes the average value of the sequence $\tilde{r}(t)$. The parameter $\lambda$=100 determines the sharpness of the transition from diffuse to specular.

After recovering the normal, each target point's normalized sequence $\hat{r}(t)$ (based on its recovered normal) is then aligned with the reference sequence from the bidirectional reflectance distribution function chart and used to reconstruct a bidirectional reflectance distribution function.

To eliminate light/view locality problems in the above processing, locality effects are assumed to be smooth (low-frequency) over the target while normal variation over a flat target lacks any low-frequency component. After recovering the normal map as described above, its low-frequency variation is estimated and removed. This is done by fitting a second-order b-spline separately to the map's x and y components. The z component of the smooth normal is then obtained by $z^2=1-x^2-y^2$. At each surface point, a compensation rotation matrix is determined by the original normal n and its b-spline fit nb by rotating around $n_b \times n$ by an angle of –arc cos ($n \cdot n_b$). The final normal then applies this rotation to n at every surface point.

Illustrative Operation

Figure 5:
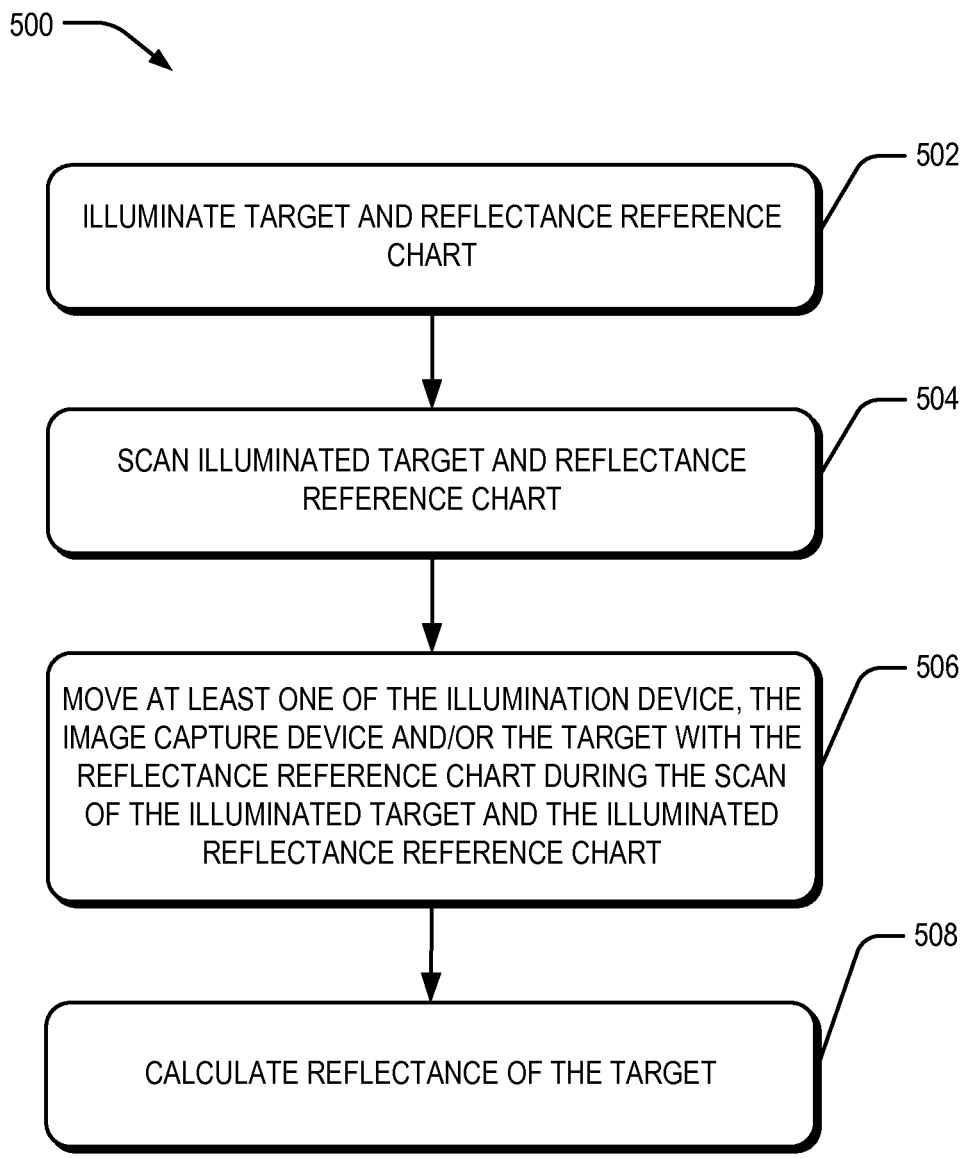
FIG. 5 is a flow diagram of an illustrative process for reflectance acquisition.

FIG. 5 is a flow diagram of a process 500 for reflectance acquisition. The process 500 is illustrated as a collection of blocks in a logical flow graph, which represent a sequence of operations that can be implemented in hardware, software, or a combination thereof. In the context of software, the blocks represent computer-executable instructions that, when executed by one or more processors, cause the one or more processors to perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process. Other processes described throughout this disclosure shall be interpreted accordingly.

At 502, the target 110 and the reflectance reference chart 108 are illuminated with the light source 112, 202. The reflectance reference chart 108 and the target 110 are in fixed positions relative to each other.

At 504, the illuminated target 110 and the illuminated reflectance reference chart 108 are scanned in at least one scanning direction with an image capture device 102.

At 506, at least one of the light source 112, 202, the image capture device 102, and the target 110 with the reflectance reference chart 108 is moved relative to the others during the scan of the illuminated target and the illuminated reflectance reference chart.

At 510, the computing device 138 calculates reflectance of the target based at least in part on knowledge of the reflectance reference chart.

Figure 6:
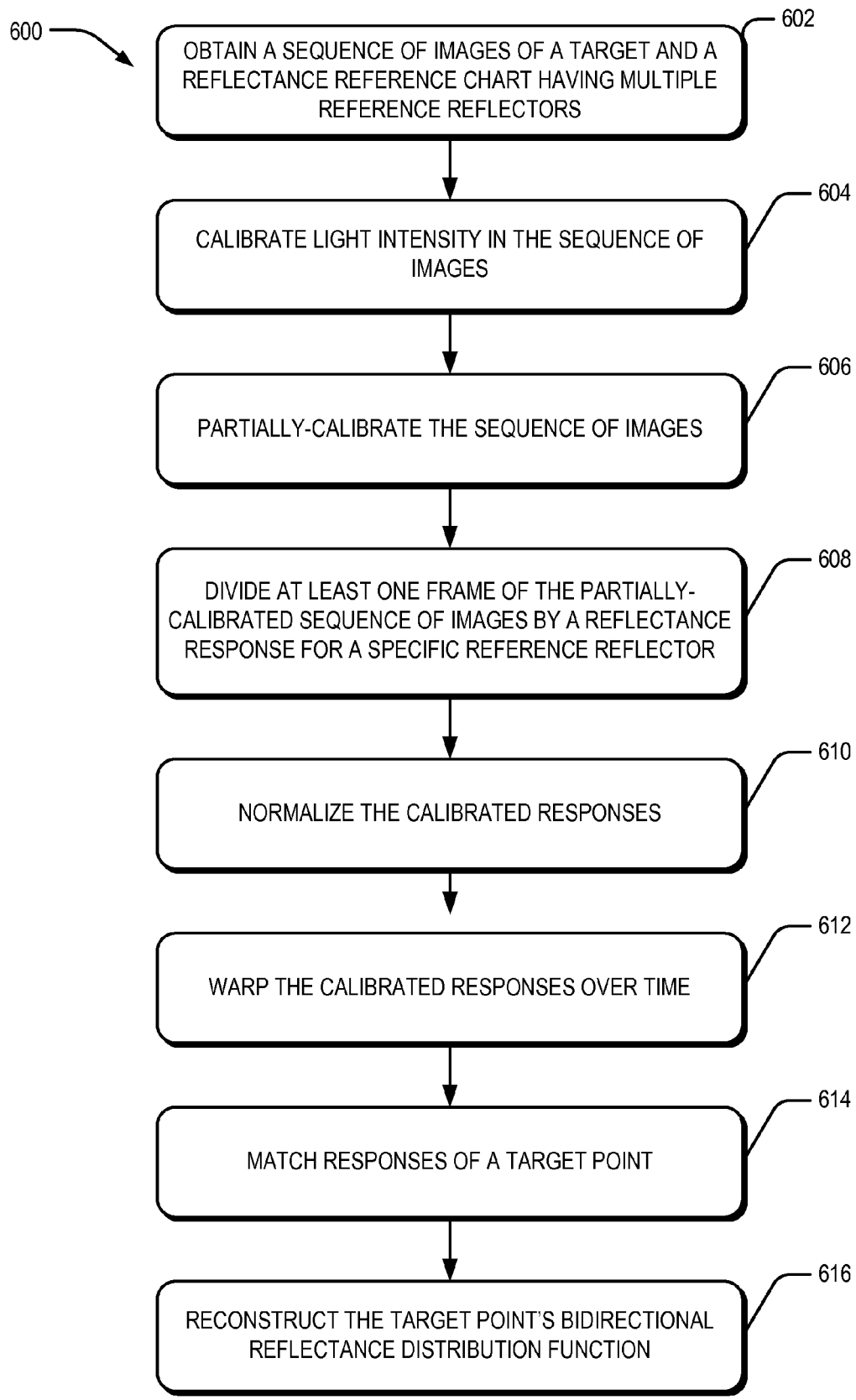
FIG. 6 is a flow diagram of another illustrative process for obtaining a spatially varying bidirectional reflectance distribution function of a target.

FIG. 6 is a flow diagram of a process 600 for obtaining a spatially varying bidirectional reflectance distribution function of a target.

At 602, a sequence of images of the target 110 and the reflectance reference chart 108 is obtained. The sequence of images is captured by the image capture device 102. The sequence of images may include at least one frame in which at least one of the target 110 and the reflectance reference chart 108 are not illuminated by the light source 112.

At 604, the light intensity in the sequence of images is at least partially-calibrated based at least on a gamma (power law) curve for the response of the image capture device 102.

At 606, the sequence of images is further partially-calibrated by removing reflected light from the background environment. The reflected light from the background environment may be removed by subtracting the frame in which light source 112 did not illuminate the target 110.

At 608, pixels of least one frame of the partially-calibrated sequence of images are divided by a reflectance response for a specific reference reflector (e.g., reference reflector 128a) to determine calibrated responses for each of the pixels or for at least some of the pixels.

At 610, the calibrated responses for each of the pixels or at least some of the pixels are normalized. The normalization of the calibrated responses may be based at least on minimum and maximum values of the calibrated responses.

At 612, calibrated responses are wrapped over time to align the calibrated response to a specular reference for each or at least some of the pixels.

At 614, responses of a target point are matched to a linear combination of Lambertian and purely specular reference responses. The linear combination of Lambertian and purely specular reference responses are weighted, and each point on the target may be matched.

At 616, the target point's bidirectional reflectance distribution function is reconstructed based at least on known reference bidirectional reflectance distribution functions. The computing device 138 may include a data base of known reference bidirectional reflectance distribution functions. Typically, the known reference bidirectional reflectance distribution functions correspond to the reflectance responses of the reference reflectors 128. In some embodiments, the same weights as those used in the linear combination of Lambertian and purely specular reference responses may be applied to the known reference bidirectional reflectance distribution functions to reconstruct the target point's bidirectional reflectance distribution function.

Illustrative Computing Device

Figure 7:
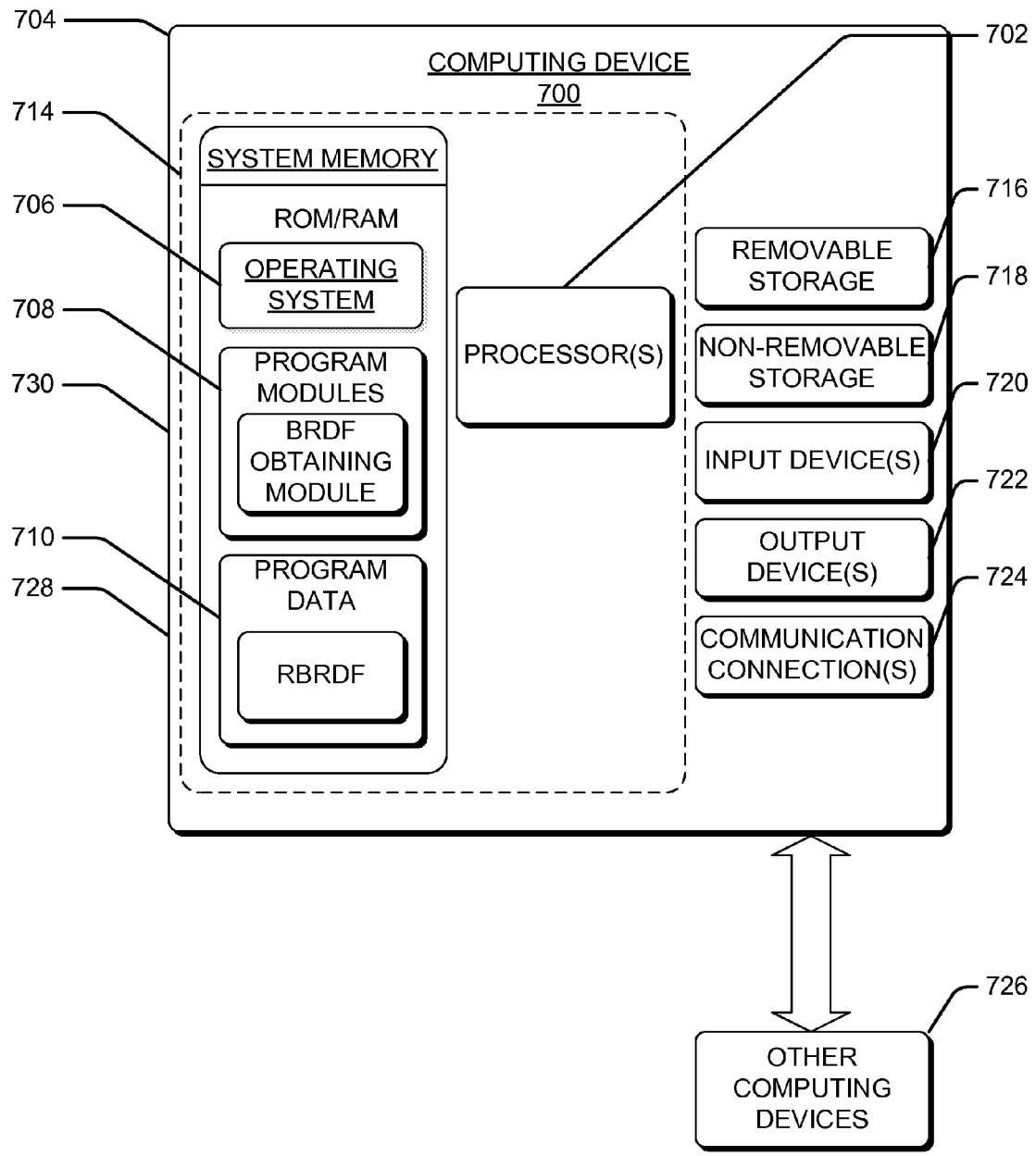
FIG. 7 is a block diagram of an illustrative computing device that may be deployed in the environment shown in FIG. 1C to obtain BDRF.

FIG. 7 shows an illustrative computing device 700 that may be used to obtain spatially varying bidirectional reflectance distribution functions. It will readily be appreciated that the various embodiments described above may be implemented in other computing devices, systems, and environments. The computing device 700 shown in FIG. 7 is only one example of a computing device (such as computing device 138) and is not intended to suggest any limitation as to the scope of use or functionality of the computer and network architectures. The computing device 700 is not intended to be interpreted as having any dependency or requirement relating to any one or combination of components illustrated in the example computing device.

In one configuration, the computing device 700 may include at least one processing unit 702 and system memory 704. Depending on the exact configuration and type of computing device, the system memory 604 may be volatile (such as RAM), non-volatile (such as ROM, flash memory, etc.) or some combination of the two. The system memory 704 typically includes an operating system 706, one or more program modules 708, and may include program data 710. The computing device 700 is of a very basic configuration demarcated by a dashed line 714.

The computing device 700 may have additional features or functionality. For example, the computing device 700 may also include additional data storage devices (removable and/or non-removable) such as, for example, magnetic disks, optical disks, or tape. Such additional storage is illustrated in FIG. 7 by removable storage 716 and non-removable storage 718. Computer-readable media may include, at least, two types of computer-readable media, namely computer storage media and communication media. Computer storage media may include volatile and non-volatile, removable, and non-removable media implemented in any method or technology for storage of information, such as computer readable instructions, data structures, program modules, or other data. The system memory 704, the removable storage 716 and the non-removable storage 718 are all examples of computer storage media. Computer storage media includes, but is not limited to, RAM, ROM, EEPROM, flash memory or other memory technology, CD-ROM, digital versatile disks (DVD), or other optical storage, magnetic cassettes, magnetic tape, magnetic disk storage or other magnetic storage devices, or any other non-transmission medium that can be used to store the desired information and which can be accessed by the computing device 700. Any such computer storage media may be part of the computing device 700. Moreover, the computer-readable media may include computer-executable instructions that, when executed by the processor(s) 702, perform various functions and/or operations described herein.

In contrast, communication media may embody computer-readable instructions, data structures, program modules, or other data in a modulated data signal, such as a carrier wave, or other transmission mechanism. As defined herein, computer storage media does not include communication media.

The program data 710 may include, among other things, reference bidirectional reflectance distribution functions 728. The reference bidirectional reflectance distribution functions 728 correspond to reflectance responses of the reference reflectors 128.

The program modules 708 may include, among other things, a BRDF obtaining module 730. The BRDF obtaining module 730 employs algorithms for, among other things, analyzing the sequence of images from the image capture device 102 and for obtaining a spatially varying bidirectional reflectance distribution function of the target 110 based at least on the reference bidirectional reflectance distribution functions 730.

The computing device 700 may also have input device(s) 720 such as keyboard, mouse, pen, voice input device, touch input device, etc. Output device(s) 722 such as a display, speakers, printer, etc. may also be included. These devices are well known in the art and are not discussed at length here.

The computing device 700 may also contain communication connections 724 that allow the device to communicate with other computing devices 726, such as over a network. These networks may include wired networks as well as wireless networks. The communication connections 724 are one example of communication media.

It is appreciated that the illustrated computing device 700 is only one example of a suitable device and is not intended to suggest any limitation as to the scope of use or functionality of the various embodiments described. Other well-known computing devices, systems, environments and/or configurations that may be suitable for use with the embodiments include, but are not limited to personal computers, server computers, hand-held or laptop devices, multiprocessor systems, microprocessor-base systems, set top boxes, game consoles, programmable consumer electronics, network PCs, minicomputers, mainframe computers, distributed computing environments that include any of the above systems or devices, and/or the like.

CONCLUSION

Although the techniques have been described in language specific to structural features and/or methodological acts, it is to be understood that the appended claims are not necessarily limited to the specific features or acts described. Rather, the specific features and acts are disclosed as exemplary forms of implementing such techniques.

What is claimed is:

1. A reflectance measurement system, comprising:
   an illumination device configured to provide a uniform band of light over at least one of a length that spans the target or a length that spans a reflectance reference chart having a plurality of different reference reflectors fixed relative to a target in known relative positions; and
   an image capture device configured to capture a sequence of images of at least a portion of the reflectance reference chart and at least a portion of the target during a scan of the target, wherein at least one of:
      the illumination device,
      the image capture device, or
      the reflectance reference chart fixed relative to the target
   is configured for motion relative to at least one respective other of the illumination device, the image capture device, and the reflectance reference chart fixed relative to the target, during a scan of the target;
   at least one processor;
   at least one computer storage medium having instructions stored therein, the instructions, when executed by the at least one processor, cause the at least one processor to perform acts comprising:
      obtaining a sequence of images of the target and the reflectance reference chart;
      matching calculated reflectance responses for pixels in the sequence of images to reference bidirectional reflectance distribution functions, each one of the reference bidirectional reflectance distribution functions corresponding to one of the reference reflectors; and
      reconstructing an image of the target based at least on the matched reference bidirectional reflectance distribution functions.

2. The reflectance measurement system of claim 1, wherein the plurality of reference reflectors includes at least one nearly ideal Lambertian reflector.

3. The reflectance measurement system of claim 1, wherein the plurality of reference reflectors includes multiple reference reflectors that each have a planar surface exposed to the image capture device.

4. The reflectance measurement system of claim 3, wherein the plurality of reference reflectors includes at least one reference reflector that has a surface exposed to the image capture device that is curved.

5. The reflectance measurement system of claim 1, wherein the image capture device is fixed relative to the reflectance reference chart.

6. The reflectance measurement system of claim 5, wherein the illumination device is movable relative to the image capture device and the reflectance reference chart.

7. The reflectance measurement system of claim 1, wherein the illumination device includes at least one of a fluorescent tube, an array of light emitting diodes, or an array of incandescent lights.

8. The reflectance measurement system of claim 1, wherein the image capture device is positioned to have a field-of-view that encompasses the target and the reflectance reference chart.

9. The reflectance measurement system 1, wherein the image capture device is configured to be portable and hand-held.

10. The reflectance measurement system of claim 1, further comprising a computer storage medium having stored therein a plurality of reference bidirectional reflectance distribution functions, each one of the reference bidirectional reflectance distribution functions corresponding to one of the reference reflectors.

11. At least one computer storage medium having instructions stored therein, the instructions, when executed by the at least one processor, cause the at least one processor to perform acts comprising:
   obtaining a sequence of images of a target and a reflectance reference chart having a multiple reference reflectors;
   matching calculated reflectance responses for pixels in the sequence of images to reference bidirectional reflectance distribution functions, each one of the reference bidirectional reflectance distribution functions corresponding to one of the reference reflectors; and
   reconstructing an image of the target based at least on the matched reference bidirectional reflectance distribution functions.

12. The computer storage medium claim 11, wherein the acts further comprise:
   calculating the reflectance responses for pixels in the sequence of images;
   calibrating the calculated reflectance responses; and
   warping the calibrated reflectance responses.

13. The computer storage medium claim 11, wherein the acts further comprise:
   accessing a database having the reference bidirectional reflectance distribution functions corresponding to one of the reference reflectors stored therein.

14. A method comprising:
   receiving a sequence of images of a target and a reflectance reference chart having multiple reference reflectors;
   matching calculated reflectance responses for pixels in the sequence of images to reference bidirectional reflectance distribution functions, individual ones of the reference bidirectional reflectance distribution functions corresponding to one of the reference reflectors; and
   reconstructing an image of the target based at least on the matched reference bidirectional reflectance distribution functions.

15. The method of claim 14 further comprising:
illuminating a target and a reflectance reference chart with an illumination device;
scanning the illuminated target and the illuminated reflectance reference chart with an image capture device, the target being fixed in position relative to the reflectance reference chart during the scanning;
moving at least one of the illumination device, the image capture device and the target-with-the-reflectance-reference-chart during the scanning of the illuminated target and the illuminated reflectance reference chart; and
computing reflectance of the target based at least in part on knowledge of the reflectance reference chart.

16. The method of claim 15, wherein the moving at least one of the illumination device, the image capture device and the target-with-the-reflectance-reference-chart during the scanning of the illuminated target and the illuminated reflectance reference chart comprises moving the illumination device relative to the image capture device, the target and the reflectance reference chart.

17. The method of claim 16, wherein moving the illumination device relative to the image capture device, the target and the reflectance reference chart comprises holding the image capture device in a fixed position relative to the target and the reflectance reference chart.

18. The method of claim 14, wherein a bidirectional reflectance distribution function of the target is computed independent of knowledge of a position of the illumination device and independent of knowledge of a position of the image capture device during the scanning of the target.

19. The method of claim 15, wherein the illuminating the target and the reflectance reference chart comprises uniformly illuminating at least a portion of at least one of the target and the reflectance reference chart during the scanning, the illuminated portion being generally perpendicular to a scan direction.

\* \* \* \* \*